(12) United States Patent
Samset et al.

(10) Patent No.: US 10,507,006 B2
(45) Date of Patent: Dec. 17, 2019

(54) SYSTEM AND METHOD FOR TRACKING AN INVASIVE DEVICE USING ULTRASOUND POSITION SIGNALS

(71) Applicant: General Electric Company, Schenectady, NY (US)

(72) Inventors: Eigil Samset, Oppegård (NO); Geir Ultveit Haugen, Stabekk (NO)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 1246 days.

(21) Appl. No.: 14/141,752

(22) Filed: Dec. 27, 2013

(65) Prior Publication Data
US 2015/0182187 A1    Jul. 2, 2015

(51) Int. Cl.
*A61B 8/08* (2006.01)
*A61B 8/12* (2006.01)
*A61B 8/00* (2006.01)
*A61B 34/20* (2016.01)
*A61B 90/00* (2016.01)

(52) U.S. Cl.
CPC ............. *A61B 8/0841* (2013.01); *A61B 8/12* (2013.01); *A61B 8/4227* (2013.01); *A61B 8/4263* (2013.01); *A61B 8/4281* (2013.01); *A61B 8/4416* (2013.01); *A61B 8/4472* (2013.01); *A61B 8/4483* (2013.01);
(Continued)

(58) Field of Classification Search
CPC ..... A61B 8/5261; A61B 8/5207; A61B 8/463; A61B 8/4494; A61B 8/4472; A61B 8/4416; A61B 8/4281; A61B 8/4263; A61B 8/4227; A61B 8/12; A61B 34/20; A61B 8/4483; A61B 2090/3966; A61B 2090/3929; A61B 2090/3784;
(Continued)

(56) References Cited

U.S. PATENT DOCUMENTS 6,246,898 B1 * 6/2001 Vesely ................. A61B 5/0422
600/424
6,456,567 B1    9/2002 Blevins et al.
(Continued)

FOREIGN PATENT DOCUMENTS

EP    0812568 A2    12/1997
EP    1374792 A1    1/2004
(Continued)

OTHER PUBLICATIONS

International Search Report and Written Opinion from corresponding PCT application No. PCT/US2014/051088; 15 pages.
(Continued)

*Primary Examiner* — Baisakhi Roy
*Assistant Examiner* — Patrick M Mehl
(74) *Attorney, Agent, or Firm* — Dean D. Small; The Small Patent Law Group, LLC

(57) ABSTRACT

A system and method for tracking an invasive device includes a localization system configured to be externally attached to a patient. The localization system includes a transducer module including a plurality of transducer elements. The system and method includes an invasive device including at least one device transducer element. The invasive device is configured to either transmit ultrasound position signals to the transducer module or receive ultrasound position signals from the transducer module.

21 Claims, 9 Drawing Sheets

(52) U.S. Cl.
CPC ............ *A61B 8/4494* (2013.01); *A61B 8/463* (2013.01); *A61B 8/5207* (2013.01); *A61B 8/5261* (2013.01); *A61B 34/20* (2016.02); *A61B 2034/2063* (2016.02); *A61B 2034/2072* (2016.02); *A61B 2090/363* (2016.02); *A61B 2090/364* (2016.02); *A61B 2090/3784* (2016.02); *A61B 2090/3929* (2016.02); *A61B 2090/3966* (2016.02)

(58) Field of Classification Search
CPC ........ A61B 2090/364; A61B 2090/363; A61B 2034/2072; A61B 2034/2063
See application file for complete search history.

(56) References Cited

U.S. PATENT DOCUMENTS

| | | |
|---|---|---|
| 8,099,153 B2 | 1/2012 | Boese |
| 8,131,041 B2 | 3/2012 | Ter Mors |
| 2003/0055308 A1* | 3/2003 | Friemel ............... A61B 8/14 600/15 |
| 2003/0158477 A1 | 8/2003 | Panescu |
| 2005/0080334 A1 | 4/2005 | Willis |
| 2008/0234570 A1 | 9/2008 | Gerard et al. |
| 2008/0287803 A1* | 11/2008 | Li ............... A61B 5/06 600/466 |
| 2010/0191101 A1* | 7/2010 | Lichtenstein ........ A61B 5/06 600/424 |

FOREIGN PATENT DOCUMENTS

| | | |
|---|---|---|
| GB | 2331365 A | 5/1999 |
| WO | 9958055 A1 | 11/1999 |

OTHER PUBLICATIONS

Hata et al., Development of a Frameless and Armless Stereotactic Neuronavigation System with Ultrasonographic Registration, Neurosurgery, vol. 41, No. 3, Sep. 1997, 7 pages.

* cited by examiner

SYSTEM AND METHOD FOR TRACKING AN INVASIVE DEVICE USING ULTRASOUND POSITION SIGNALS

FIELD OF THE INVENTION

This disclosure relates generally to a system and method for tracking an invasive device using ultrasound position signals.

BACKGROUND OF THE INVENTION

During an invasive procedure, a clinician is concerned about the location and trajectory of an invasive device inserted into a patient. The clinician needs to clearly understand exactly where the invasive device is located and how it is positioned for both patient safety and clinical effectiveness.

There are multiple techniques that are currently used for determining the position of an invasive device. The invasive device may be tracked with an electromagnetic tracking system. The electromagnetic tracking system provides real-time feedback about the position of the invasive device, but it requires significantly more equipment. For example, the electromagnetic tracking system requires an electromagnetic field generator that is positioned outside the patient and one or more sensor coils attached to the invasive device being tracked. Electromagnetic fields are susceptible to distortion that may arise from environmental factors such as electrical equipment and/or conductors positioned near that patient and/or the field generator.

Another conventional technique involves obtaining position information from an X-ray fluoroscopy system. The X-ray fluoroscopy system may either be on during the whole procedure or it may be turned on only during periods of time where the clinician adjusts the position of the invasive device. Either way, the X-ray fluoroscopy system exposes both the patient and the clinician to ionizing radiation. Additionally, the images provided by an X-ray fluoroscopy system only contain 2D data. As such, it may be difficult for the clinician to accurately determine the position of the invasive device, particularly when it is moved in a direction that is out-of-plane of the X-ray fluoroscopy image. While this drawback may be partially overcome by obtaining X-ray fluoroscopy images at multiple different angles, it is still difficult for the clinician to understand the exact position of the invasive device based on data from a X-ray fluoroscopy system.

A commonly used technique to guide minimally invasive procedures is to combine two different imaging modalities. For example, X-ray fluoroscopy may be used for overview and invasive device visualization, while 3D ultrasound may be used for detailed anatomical structure assessment and 3D navigation. When two different imaging modalities are used in combination, it is important for the user to understand their relation to each other. This can be achieved by image-overlay or aligned side-by-side views. Generating such views is only possible if the relative position and orientation between the two images of different modalities are known.

For these and other reasons an improved system and technique for tracking the position of an invasive device is desired.

BRIEF DESCRIPTION OF THE INVENTION

The above-mentioned shortcomings, disadvantages and problems are addressed herein which will be understood by reading and understanding the following specification.

In an embodiment, a system for tracking a position of an invasive device includes a localization system. The localization system includes a substrate configured to be externally attached to a patient, an ultrasound transducer module attached to the substrate, wherein the ultrasound transducer module is configured to either transmit or receive ultrasound signals. The localization system also includes a connector device electrically connected to the ultrasound transducer module. The invasive device includes at least one device transducer element. The invasive device is configured to either transmit the ultrasound position signals to the ultrasound transducer module or receive the ultrasound position signals from the ultrasound transducer module.

In another embodiment, a system for tracking a position of an invasive device in a patient includes a localization system. The localization system includes a substrate configured to be externally attached to the patient, an ultrasound transducer module attached to the substrate, wherein the ultrasound transducer module is configured to either transmit or receive ultrasound position signals. The localization system also includes a connector device electrically connected to the ultrasound transducer module. The invasive device includes at least one device transducer element. The system includes a processing unit in electronic communication with the ultrasound transducer module and the at least one device transducer element. The processor is configured to receive a non-ultrasound image of the patient. The non-ultrasound image represents includes at least a portion of the localization system. The processor is configured to identify a position of the ultrasound transducer module in the non-ultrasound image. The processor is configured to determine a position of the invasive device with respect to the non-ultrasound image based on the ultrasound position signals communicated between the ultrasound transducer module and the at least one device transducer element. The processor is configured to display, on the display device, a representation of the invasive device on the non-ultrasound image based on the determined position of the invasive device with respect to the non-ultrasound image.

In another embodiment, a method of tracking a position of an invasive device with respect to a non-ultrasound image includes attaching a plurality of transducer elements to the outside of a patient, acquiring non-ultrasound data of the patient, wherein the non-ultrasound data includes the plurality of transducer elements. The method includes positioning an invasive device inside the patient, wherein the invasive device includes a device transducer element. The method includes generating an image based on the non-ultrasound data, identifying a plurality of locations representing the plurality of transducer elements in the non-ultrasound image. The method includes determining a position of the invasive device with respect to the non-ultrasound image based on the ultrasound position signals communicated between the device transducer element and the plurality of transducer elements and based on the identified locations representing the plurality of transducer elements in the non-ultrasound image. The method also includes displaying a representation of the invasive device on the non-ultrasound image based on the determined position of the invasive device.

Various other features, objects, and advantages of the invention will be made apparent to those skilled in the art from the accompanying drawings and detailed description thereof.

DETAILED DESCRIPTION OF THE INVENTION

Figure 1:
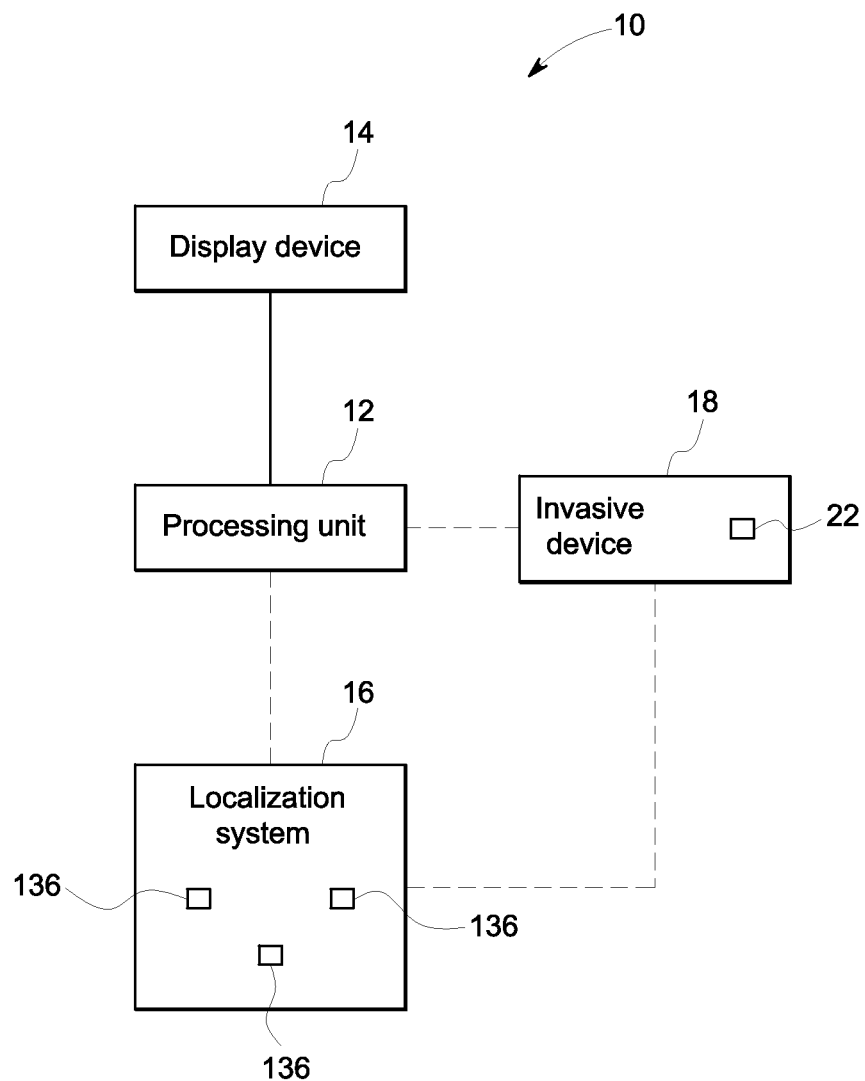
FIG. 1 is a schematic representation of a system for tracking a position of an invasive device in accordance with an embodiment.

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention. In the drawings, like elements are identified with like identifiers.

FIG. 1 is a schematic representation of a system 10 for tracking a position of an invasive device 18 in accordance with an embodiment. The system 10 includes a processing unit 12, a display device 14, a localization system 16, and an invasive device 18. The display device 14 may comprise a monitor, a display, an LED flat screen, an OLED screen, a projector, or any other device capable of displaying an image. The processing unit 12 is connected to the display device 14. The processing unit 12 may include a central processing unit (CPU), one or more ASICs, one or more microcontrollers, logic circuits, or any other circuit or processing unit capable of executing a set of commands or instructions. The processing unit 12 is in communication with at least one of the localization system 16 and the invasive device 18. The connections between the processing unit 12 and the localization system 16 and between the processing unit 12 and the invasive device 18 are shown in a dashed line. The dashed line indicates that the processing unit 12 may be in communication with one or both of the invasive device 18 and the localization system 16.

The invasive device 18 may include any type of device that is configured to be inserted into a patient. For example, the invasive device 18 may include an ultrasound probe, a catheter, or any other tool or device adapted to be inserted into the patient. For embodiments where the invasive device 18 is an ultrasound probe, the ultrasound probe may include a transesophageal (TEE) probe, a vaginal probe, a transrectal probe, a laprascopic probe, or an intracardiac (ICE) probe. The invasive device 18 includes at least one device transducer element 22. The device transducer element 22 is configured to transmit and/or receive ultrasound energy. The device transducer element 22 may comprise any material that is adapted to convert a signal into acoustic energy and/or convert acoustic energy into a signal. The device transducer element 22 may be a piezoelectric material, such as lead zirconate titanate (PZT), or a capacitive micromachined ultrasound transducer (CMUT) according to exemplary embodiments. The invasive device 18 may include more than one device transducer element 22. For example, the invasive device 18 may include two or more device transducer elements 22. The device transducer elements 22 may be arranged in an array, or the device transducer elements 22 may be separated from each other on the invasive device 18.

The localization system 16 includes a plurality of transducer elements 136. The plurality of elements 136 may be attached to the substrate 122 (shown in FIG. 3). The substrate 122 may be flexible to conform to the surface of a patient or the substrate 122 may be rigid. The substrate 122 is configured secure the plurality of transducer elements 136 to the patient. According to some embodiments, the substrate 122 may comprise a band configured to be wrapped about the patient or the substrate 122 may be shaped like a vest that is configured to be worn by the patient. It should be appreciated that the substrate 122 may be any other shape or dimension as well according to other embodiments. The invasive device 18 may be configured to transmit ultrasound position signals to the localization system 16. According to an embodiment, the localization system 16 may be configured to transmit ultrasound position signals to the invasive device 18. Additional details about the ultrasound position signals and both the invasive device 18 and the localization system 16 will be described hereinafter.

Figure 2:
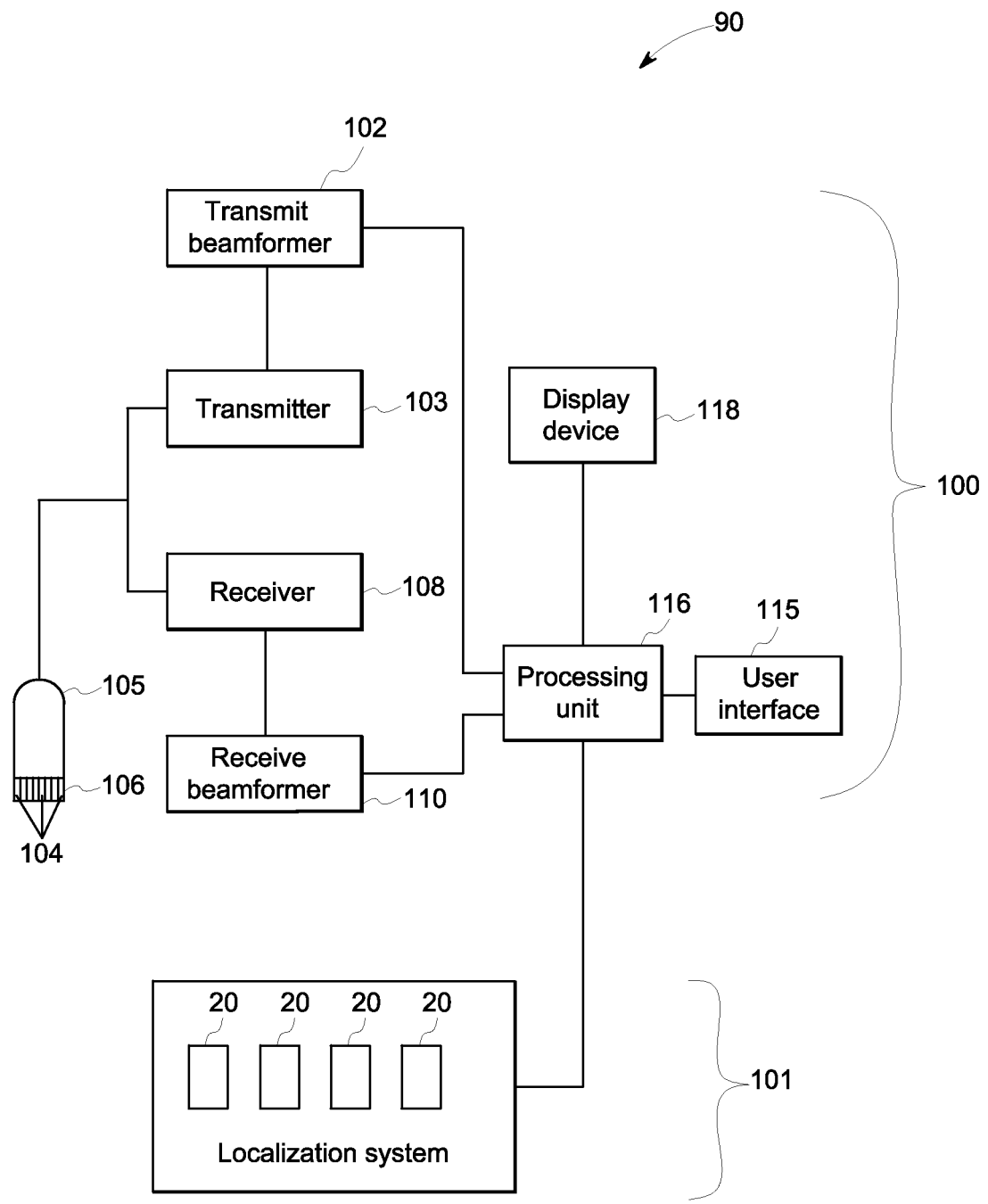
FIG. 2 is a schematic representation of a system for tracking a position of an invasive device in accordance with an embodiment.

FIG. 2 is a schematic diagram of a system 90 for tracking a position of an invasive device in a patient in accordance with an embodiment. The system 90 includes an ultrasound system 100 and a localization system 101. Couplings between various components of the ultrasound imaging system 100 and the localization system 101 are indicated on the schematic diagram by lines connecting the individual components. Each line may represent either a physical coupling, such as a wire or a fiber optic connection, or the lines may represent a wireless coupling between components. The lines may represent the way data or signals may travel through the various components of the system 90.

The ultrasound imaging system 100 includes a transmit beamformer 102 that transmits a signal to a transmitter 103 which in turn drives transducer elements 104 within an array 106 to emit pulsed ultrasonic signals into a structure, such as a patient (not shown). The transducer elements 104 may comprise any material that is adapted to convert a signal into acoustic energy and/or convert acoustic energy into a signal. Each transducer element 104 may be a piezoelectric material, such as lead zirconate titanate (PZT), or a capacitive micromachined ultrasound transducer (CMUT) according to exemplary embodiments. An ultrasound probe 105 includes both the array 106 and the transducer elements 104. The ultrasound probe 105 may be an electronically steerable 2D array according to an embodiment. According to other embodiments, the ultrasound probe 105 may include a different configuration, including a mechanical 3D probe, a phased array probe, or any other probe capable of acquiring ultrasound data. The pulsed ultrasonic signals are backscattered from structures in the body, like blood cells or muscular tissue, to produce echoes that return to the transducer elements 104. A coupling material such as acoustic gel may be used to enhance the acoustic coupling between the transducer elements 104 and the tissue being imaged. The echoes are converted into electrical signals by the transducer elements 104 and the electrical signals are received by a receiver 108. The electrical signals representing the received echoes are passed through a receive beamformer 110 that outputs ultrasound data. The ultrasound data may include 3D ultrasound data acquired from a volume, 2D ultrasound data acquired from a plane, or a plane reconstructed from a 3D ultrasound volume. A user interface 115 may be used to control operation of the ultrasound imaging system 100. For example, the user interface 115 may be used to control the input of patient data, to change a scanning or display parameter, and the like.

The ultrasound imaging system 100 also includes a processing unit 116 to control the components of the ultrasound imaging system 100 and to process the ultrasound data for display on a display device 118. The processing unit 116 may include one or more separate processing components. For example, the processing unit 116 may include a graphics processing unit (GPU) according to an embodiment. Having a processing unit that includes a GPU may advantageous for computation-intensive operations, such as volume-rendering, which will be described in more detail hereinafter. The processing unit 116 may also include one or more modules, each configured to process received ultrasound data according to a specific mode. Each module may include dedicated hardware components that are configured to process ultrasound data according to a particular mode. For example, the processing unit 116 may include a color-flow module configured to generate a color-flow image and a B-mode module configured to generate a B-mode image. Other embodiments may not include separate modules within the processing unit 116 for processing different modes of ultrasound data. The processing unit 116 may be configured to implement instructions stored on a non-transitory computer-readable medium. The computer-readable medium may include any type of disk including floppy disks, optical disks, CD-ROMs, magneto-optical disks, ROMs, RAMs, EPROMs, EEPROMs, flash memory, magnetic or optical cards, or any other type of media suitable for storing electronic instructions.

The processing unit 116 is coupled to the transmit beamformer 102, the transmitter 103, the ultrasound probe 105, the receiver 108, the receive beamformer 110, the user interface 115 and the display device 118. The processing unit 116 may be hard-wired to the aforementioned components or the processing unit 116 may be in electronic communication through other techniques including wireless communication. The display device 118 may include a screen, a monitor, a flat panel LED, a flat panel LCD, any other device configured to display an image.

The processing unit 116 may be adapted to perform one or more processing operations on the ultrasound data. Other embodiments may use multiple processing units to perform various processing tasks. The processing unit 116 may also be adapted to control the acquisition of ultrasound data with the ultrasound probe 105. The ultrasound data may be processed in real-time during a scanning session as the echo signals are received. For purposes of this disclosure, the term "real-time" is defined to include a process performed with no intentional lag or delay. The term "real-time" is further defined to include processes performed with less than 0.5 seconds of delay. An embodiment may update the displayed ultrasound image at a rate of more than 20 times per second. Ultrasound data may be acquired even as images are being generated based on previously acquired data and while a live or dynamic image is being displayed. Then, as additional ultrasound data is acquired, additional frames or images generated from more-recently acquired ultrasound data are sequentially displayed. Additionally or alternatively, the ultrasound data may be stored temporarily in a buffer (not shown) during a scanning session and processed in less than real-time in a live or off-line operation. Some embodiments of the invention may include multiple processing units (not shown) to handle the processing tasks. For example, a first processing unit may be utilized to demodulate and decimate the ultrasound signal while a second processing unit may be used to further process the data prior to displaying an image. It should be appreciated that other embodiments may use a different arrangement of processing units.

The processing unit 116 may be used to generate a volume-rendering from ultrasound data of a volume acquired by the ultrasound probe 105. The ultrasound data may contain a value or intensity assigned to each of a plurality of voxels, or volume elements. In 3D ultrasound data, each of the voxels is assigned a value determined by the acoustic properties of the tissue or fluid corresponding to that particular voxel. The 3D ultrasound data may include B-mode data, color-flow data, strain mode data, tissue-velocity data, etc. according to various embodiments. The ultrasound imaging system 100 shown may be a console system, a cart-based system, or a portable system, such as a hand-held or laptop-style system according to various embodiments. According to various embodiments, the localization system 101 may include one or more skin patches 20 adapted to be attached to the patient. Several examples of exemplary skin patches will be described according to various embodiments hereinafter.

Figure 3:
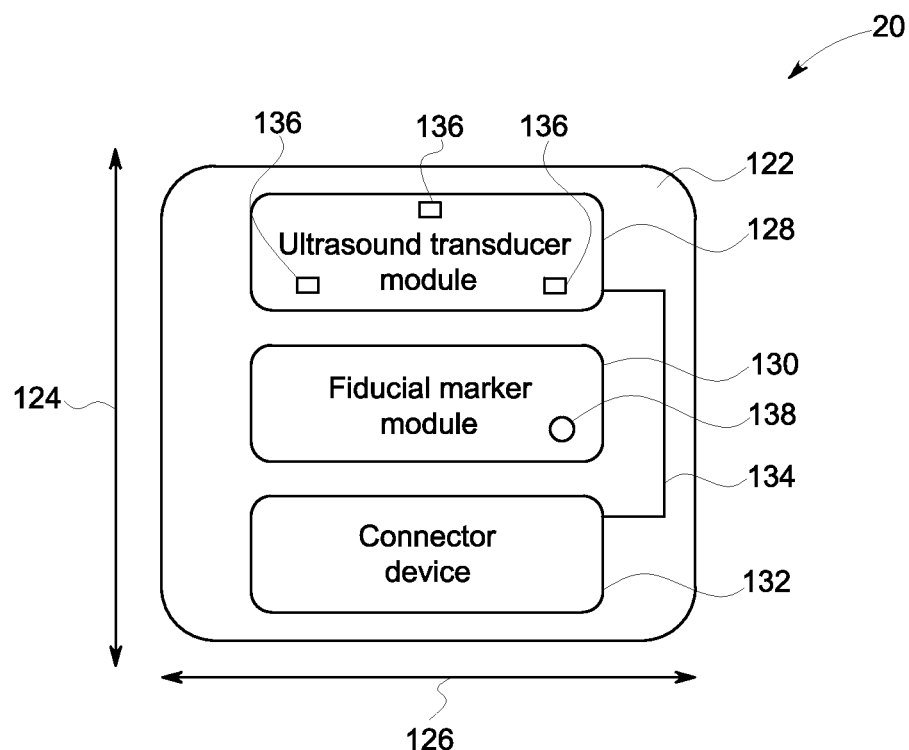
FIG. 3 is a schematic representation of a skin patch in accordance with an embodiment.

FIG. 3 is a schematic representation of the skin patch 20 according to an embodiment. The skin patch 20 includes a substrate 122 that is adapted to be attached to a patient. According to an embodiment, the substrate 122 may be approximately 2.5 cm in a length direction 124 and approximately 2 cm in a width direction 126. The substrate 122 also has a thickness direction perpendicular to both the width direction 124 and the length direction. The thickness direction is not visible in FIG. 3. It should be appreciated that the substrate 122 may be different dimensions according to other embodiments. Additionally, according to an embodiment, the substrate 122 may include an adhesive backing adapted to attach the skin patch 20 to the patient.

The skin patch 20 includes an ultrasound transducer module 128, a fiducial marker module 130, and a connector device 132. Other embodiments may include skin patches without fiducial markers. The ultrasound transducer module is electrically connected to the connector device 132 via electrical connection 134. The ultrasound transducer module 128 may include one or more transducer elements 136. Each transducer element 136 may comprise a piezoelectric material, a CMUT, or any other material that is adapted to at least one of transmit or receive ultrasound energy. The transducer elements 136 are spaced apart from each other according to the embodiment shown in FIG. 3. The connector device 132 may include either a wired connection or a wireless communication module. The connector device 132 and the ultrasound transducer module 128 may be configured differently according to various embodiments. The skin patch 20 also includes a fiducial marker module 130 including at least one fiducial marker 138. The fiducial marker 138 may include a radiopaque material, such as lead or another material that would be easily visible in an X-ray image. The radiopaque material may include any "high-Z" material with a relatively high attenuation coefficient compared to human soft tissue. The fiducial marker 138 may be made of a different material for use with imaging modalities other than ultrasound. For example, the fiducial marker 138 may be configured for visibility in magnetic resonance imaging. The fiducial marker 138 may be a material such as a gold iron alloy, which is highly visible in an image acquired with a magnetic resonance imaging system. It should be appreciated that the fiducial marker may comprise a different material selected to be visible in a specific imaging modality according to other embodiments.

Figure 4:
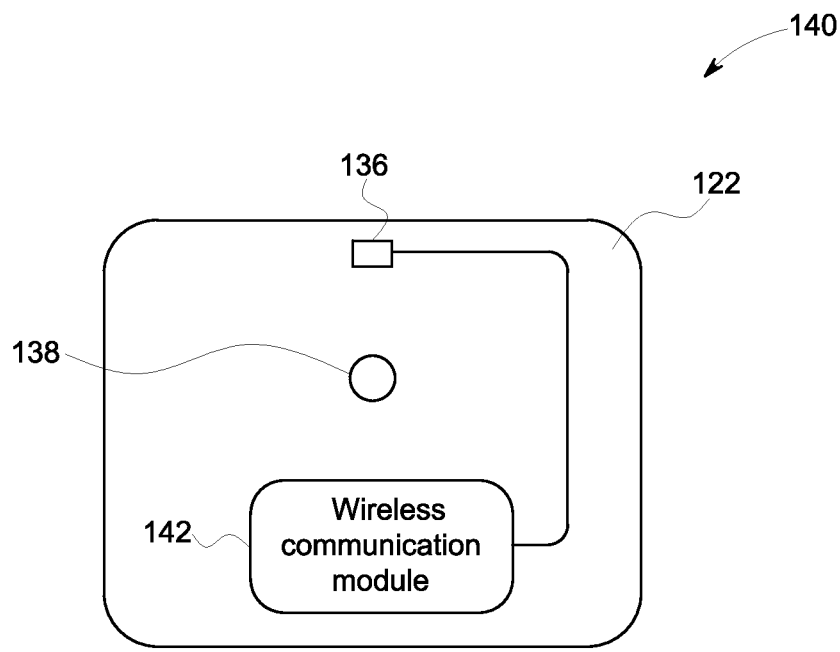
FIG. 4 is a schematic representation of a skin patch in accordance with an embodiment.

FIG. 4 is a schematic representation of a skin patch 140 according to an embodiment. The skin patch 140 includes the substrate 122, a single transducer element 136, a single fiducial marker 138 and a wireless communication module 142. The wireless communication module 142 is configured to transmit data between a processing unit, such as the processing unit 12 shown in FIG. 1, and the transducer element 136. The transducer element, the fiducial marker 138, and the wireless communication module 142 are all attached to the substrate 122. The transducer element 136 is electrically connected to the wireless communication module.

Figure 5:
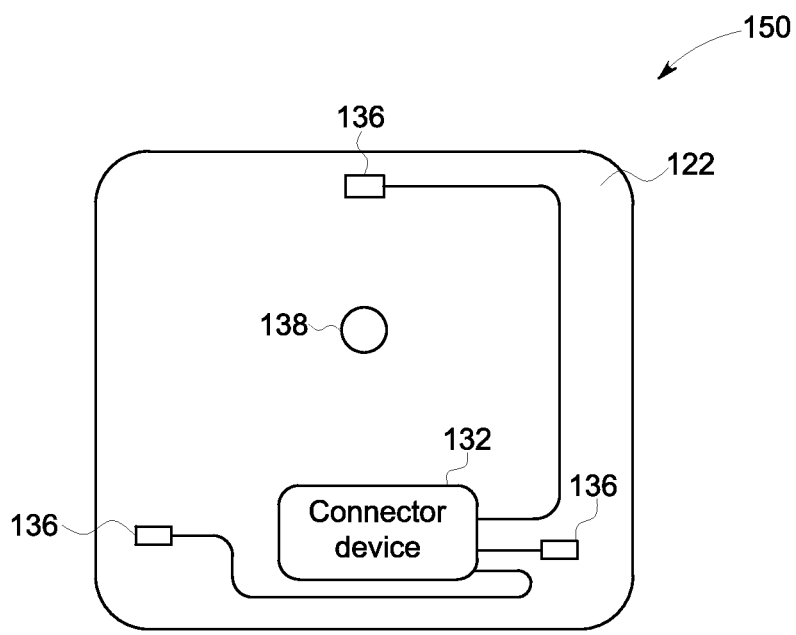
FIG. 5 is a schematic representation of a skin patch in accordance with an embodiment.

FIG. 5 is a schematic representation of a skin patch 150 according to an embodiment. The skin patch 150 includes the substrate 122, three transducer elements 136, the fiducial marker 138, and the connector device 132. The three transducer elements 136, the fiducial marker 138, and the connector device 132 are all connected to the substrate 122. The transducer elements 136 are electrically connected to the connector device 132.

Figure 6:
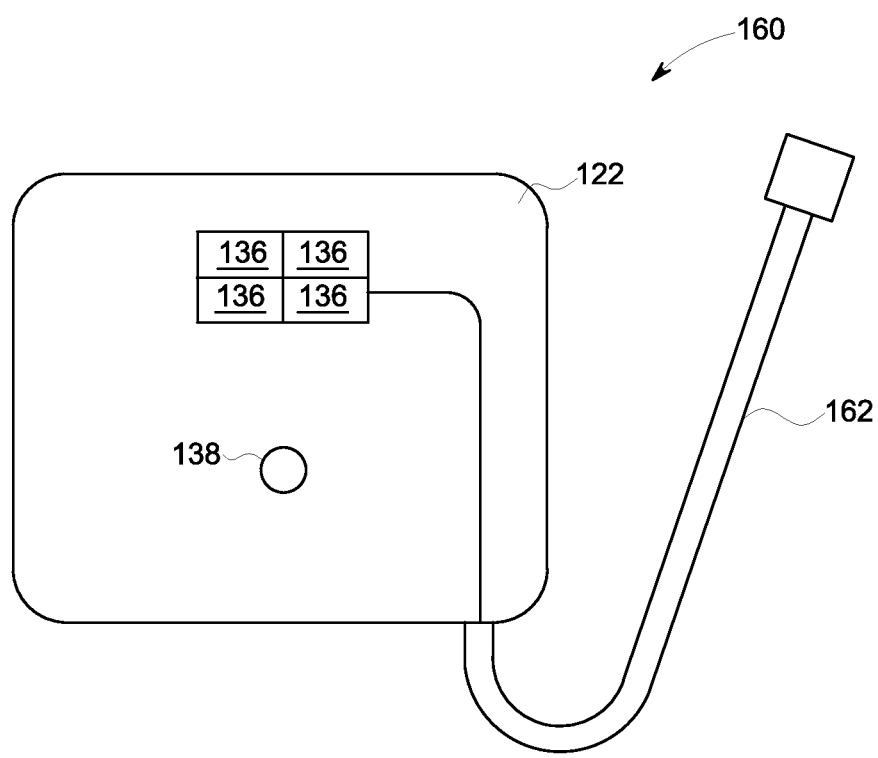
FIG. 6 is a schematic representation of a skin patch in accordance with an embodiment.

FIG. 6 is a schematic representation of a skin patch 160 in accordance with an embodiment. The skin patch 160 includes the substrate 122, four transducer elements 136, a fiducial marker 138, and a wired connection 162. The transducer elements 136 are arranged in a 2 by 2 array according to the embodiment shown in FIG. 6. The transducer elements 136, the fiducial marker 138, and the wired connection 162 are all connected to the substrate 122. The transducer elements 136 are electrically connected to the connector device 132.

Figure 7:
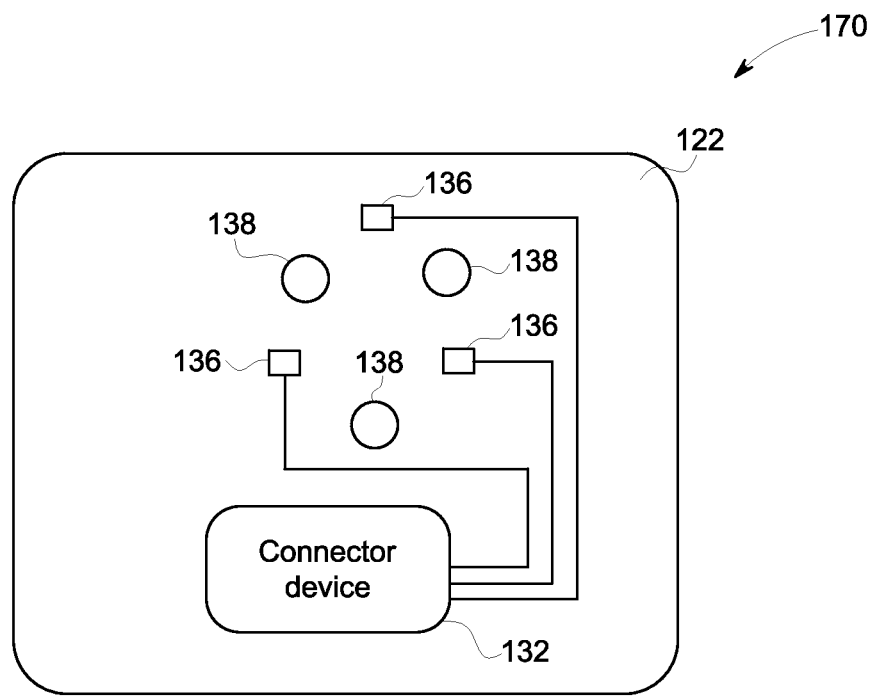
FIG. 7 is a schematic representation of a skin patch in accordance with an embodiment.

FIG. 7 is a schematic representation of a skin patch 170 in accordance with an embodiment. The skin patch 170 includes the substrate 122, three transducer elements 136, and three fiducial markers 138. The transducer elements 136, the fiducial markers 138, and the connector device 132 are all connected to the substrate 122. The transducer elements 136 are electrically connected to the connector device 132.

Figure 8:
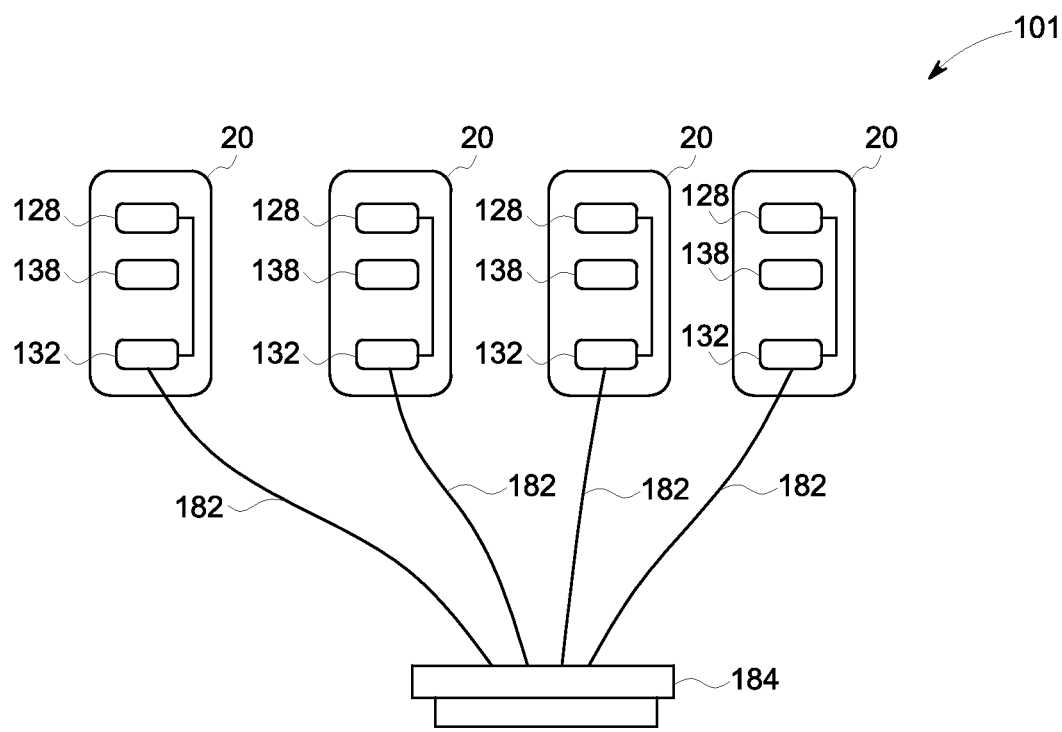
FIG. 8 is a schematic representation of a localization system in accordance with an embodiment.

FIG. 8 is a schematic representation of the localization system 16. FIG. 8 represents a more detailed view of the localization system 16 shown in FIG. 2. The localization system 101 includes 4 skin patches 20. Each of the skin patches 20 includes the ultrasound transducer module 128, the fiducial marker 138, and the connector device 132. It should be appreciated that connector device 132 may comprise a simple electrical connection, such as a wire, according to some embodiments. In the embodiment shown in FIG. 8, the connector device includes four wired connections 182. Each of the wired connections 182 connects a skin patch 20 to a connector 184. The connector 184 may be shaped and adapted to fit into a standard probe port, such as a phased array port, on an ultrasound imaging system. By configuring the connector 184 so that it is adapted to fit into a standard ultrasound probe port, it is possible to connect the localization system 101 to the ultrasound imaging system without requiring the addition of any additional hardware to the ultrasound imaging system. This allows the use of the localization system 101 with only a software or firmware update to the ultrasound imaging system.

Figure 9:
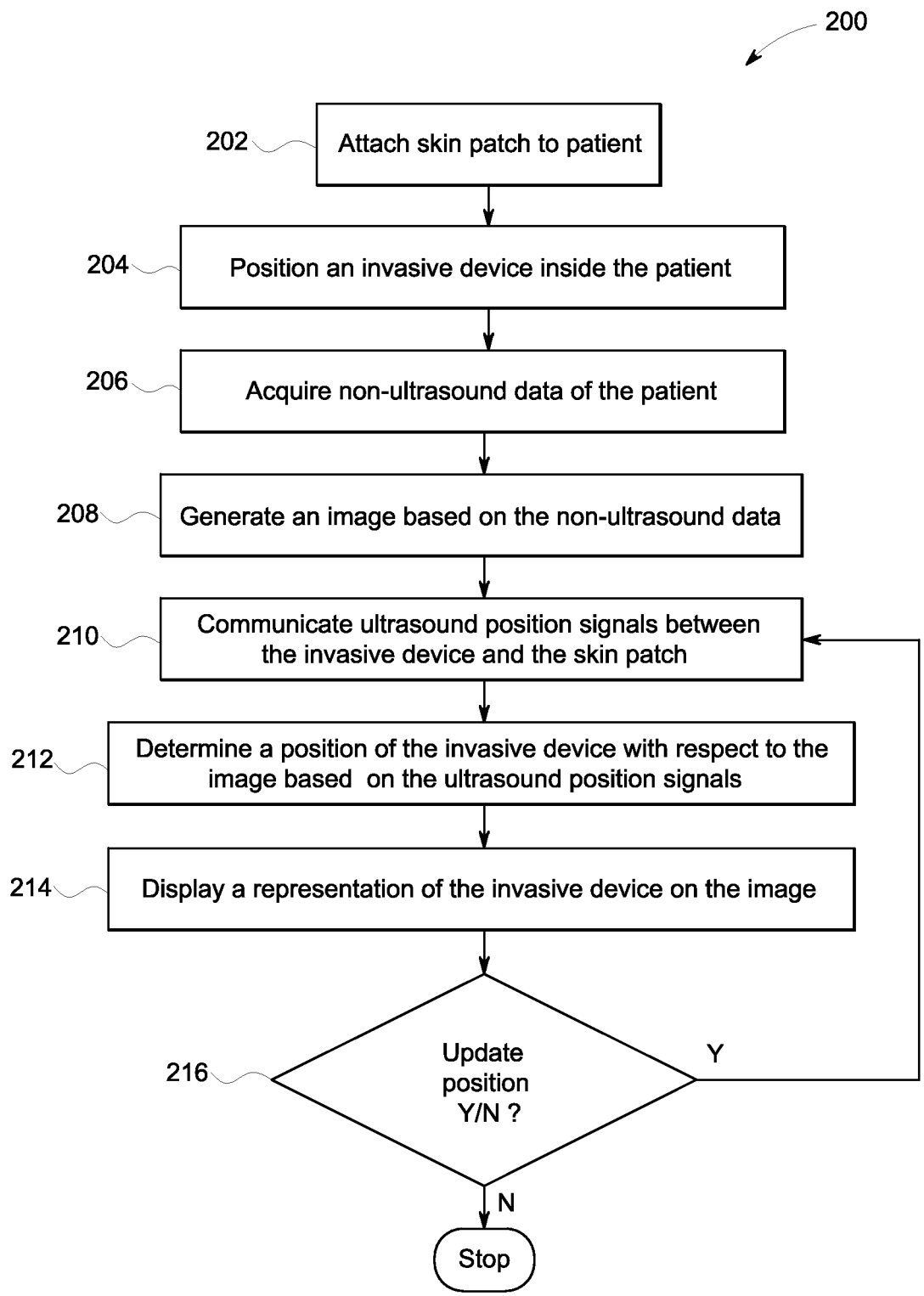
FIG. 9 is a flow chart of a method in accordance with an embodiment.

FIG. 9 is a flow chart of a method 200 in accordance with an exemplary embodiment. The individual blocks of the flow chart represent steps that may be performed in accordance with the method 200. Additional embodiments may perform the steps shown in a different sequence and/or additional embodiments may include additional steps not shown in FIG. 9. The technical effect of the method 200 is the display of a representation of an invasive device on an image acquired by a non-ultrasound imaging device based on ultrasound position signals communicated between the invasive device and one or more skin patches. The method 200 will first be described according to an embodiment where the localization system 16 comprises a plurality of skin patches 20 as shown in FIG. 8.

Figure 10:
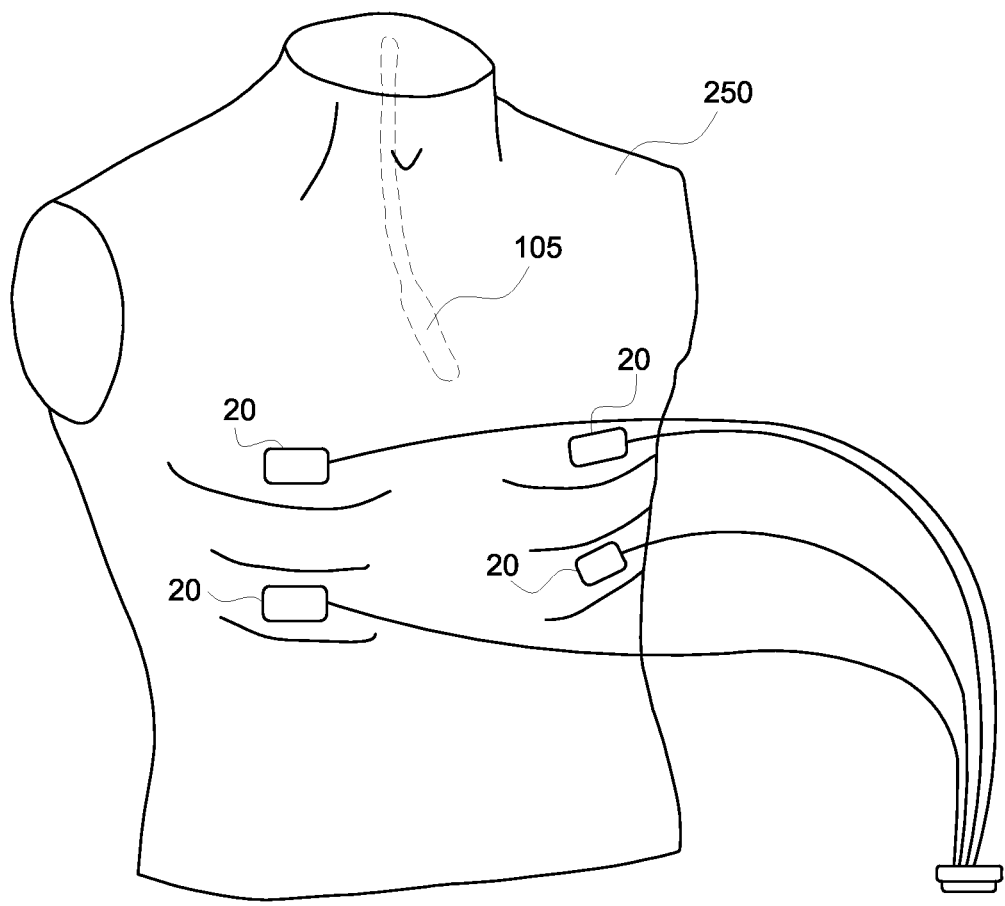
FIG. 10 is a schematic representation of four skin patches placed on a patient's torso in accordance with an embodiment.

Referring to FIGS. 1 and 9, at step 202, a clinician attaches one or more skin patches to a patient 250. FIG. 10 is a schematic representation of four skin patches 20 placed on a patient's torso in accordance with an embodiment. According to an exemplary embodiment, the clinician may attach four skin patches 20 to the patient 250 in generally the positions represented in FIG. 10. The skin patches 20 may be placed in between the patient's ribs in order to facilitate the transmission of ultrasound energy between the skin patches 20 and the probe 105. Different embodiments may use a different number of skin patches and/or the skin patches may be placed differently than shown in the embodiment of FIG. 10.

At step 204, an invasive device is positioned inside the patient. As described previously, the invasive device includes at least one transducer element. The invasive device may include any type of device that is configured to be inserted into the patient's body, such as a catheter. The invasive device may also include an ultrasound probe such as a transesophageal (TEE) probe, a vaginal probe, a transrectal probe, a laproscopic probe, or an intracardiac (ICE) probe. For embodiments where the invasive device is an ultrasound probe, the ultrasound probe may include additional transducer elements used for tracking the probe, or the probe may rely instead on just the elements in the array that are also used for acquiring ultrasound image data. FIG. 10 illustrates an embodiment where the invasive device is a TEE probe 105 that is shown in a dashed line to represent that it is positioned inside the patient 250.

At step 206, non-ultrasound data of the patient 250 is acquired after the skin patches have been attached. Also during step 206, a non-ultrasound image is generated based on the non-ultrasound data. The non-ultrasound data may include any modality of imaging data other than ultrasound imaging data. For example, non-ultrasound data may include X-ray data, X-ray fluoroscopy data, computed tomography (CT) data, magnetic resonance imaging (MRI) data, positron emission tomography (PET) data, single photon emission computed tomography (SPECT) data, or any other kind of imaging data other than ultrasound imaging data. The method 200 will be described according to an exemplary embodiment where the non-ultrasound data comprises X-ray data.

At step 208, a processing unit, such as the processing unit 12 shown in FIG. 1, generates an image based on the non-ultrasound data. According to other embodiments, a separate processing unit may be used to generate the image based on the non-ultrasound data. A non-ultrasound image may also be accessed from a memory or database by a processing unit such as processing unit 12. According to an exemplary embodiment, the non-ultrasound image may comprise an X-ray image. At step 210, the ultrasound position signals are communicated between the device transducer element 22 and the transducer elements 136 attached to the skin patches 20. The ultrasound position signals may be communicated according to several different schemes. According to an embodiment, the invasive device 18 may transmit the ultrasound position signals which are then received by the skin patches 20. The ultrasound position signals may, for instance, comprise omnidirectional echoes that are completely unfocused. According to other embodiments where the invasive device includes multiple device transducer elements 22, processing unit 12 may control the device transducer elements 22 to transmit focused ultrasound echoes. The ultrasound position signals used for determining the position of the invasive device 18 may be transmitted at a rate of 10-30 frames per second according to an exemplary embodiment. It should be appreciated that embodiments may transmit ultrasound position signals at rates both slower than 10 frames per second and faster than 30 frames per second according to other embodiments.

According to an embodiment, the ultrasound transducer modules 128 attached to each of the skin patches 20 may be adapted to transmit the ultrasound position signals. The ultrasound position signals may then be received by the device transducer element 22 attached to the invasive device 18. Each transducer element 136 attached to the skin patches 20 may have a unique signature or time difference in order to associate data with a particular transducer element 136 on the skin patch 20. The transducer elements 136 may be assigned unique signatures by adjusting variables such as pulse shape, pulse length, and frequency. The ultrasound position signals may also be sent from the transducer elements 136 sequentially. In other words, each ultrasound position signal may be sent by a specific transducer element 136 and received by the device transducer element 22 before the next ultrasound position signal is transmitted. It is not necessary to apply unique signatures to each transducer element if the position signals are transmitted in a serial manner, but the total time required is greater than if the unique signatures are used and the ultrasound position signals are transmitted in parallel.

According to an embodiment, ultrasound position signals may be transmitted from both the ultrasound device transducer element 22 and the skin patches 20. Or, the ultrasound position signals may be transmitted from the transducer elements 136 attached to the skin patches 20. If the transducer elements 136 attached to the skin patches are assigned unique signatures, the processing unit 116 may use techniques including Fourier analysis in order to separate the different signals and associate the correct timing information with the appropriate ultrasound transducers 136.

Figure 11:
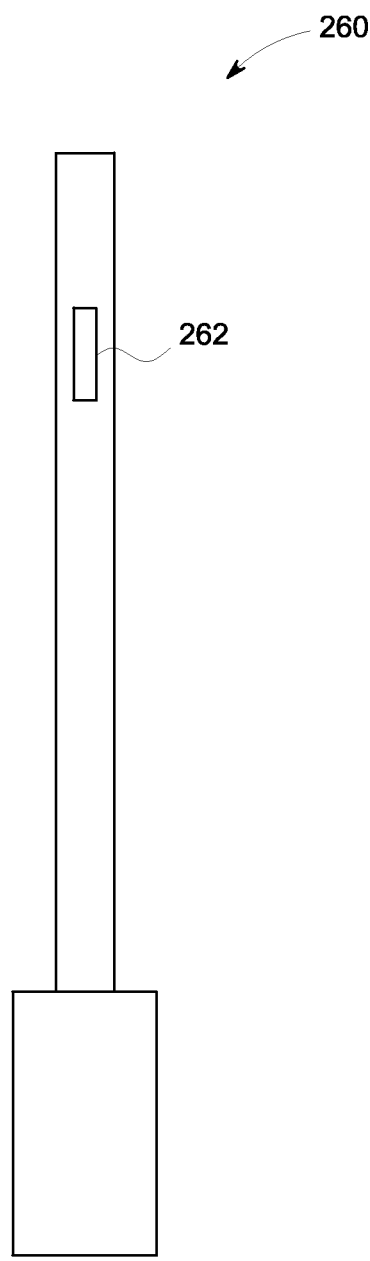
FIG. 11 is a schematic representation of a catheter in accordance with an embodiment.

In the exemplary embodiments described hereinabove, the invasive device may be a catheter similar to the one shown in FIG. 11. FIG. 11 is a schematic representation of a catheter 260 in accordance with an embodiment. The catheter 260 includes a transducer array 262 according to an embodiment. The transducer array 262 includes a plurality of device transducer elements (not shown) according to an embodiment. It should be appreciated by those skilled in the art that a different type of invasive device may be used in place of the catheter 260 in other embodiments. It should be appreciated that the transducer array 262 may function like the array 106 in the ultrasound probe 105 for communicating ultrasound position signals with the transducer elements 136 on the skin patches 20. According to other embodiments, the invasive device may only include a single device transducer element for communicating ultrasound position signals with the transducer elements 136 on the skin patches 20.

At step 212, a processing unit, such as the processing unit 12, determines a position of the invasive device 18 with respect to the image. As previously described, the image is based on non-ultrasound data and the non-ultrasound data was acquired from a region or volume including the skin patches. Each of the skin patches 20 includes a fiducial marker 138 that may be clearly identified by the processing unit 116 in the non-ultrasound data or image. As described with respect to step 210, ultrasound position signals are communicated between the invasive device 18 and the transducer elements 136 attached to the skin patches 20. The processing unit 116 may determine the position of the invasive device 18 with respect to the skin patches 20 based on the time it takes to receive the ultrasound position signal from the invasive device 18 at each respective transducer element 136 on the skin patches 20. As long as at least three of the transducer elements 136 are positioned in different three dimensional positions with respect to the invasive device 18 being tracked, the processing unit 116 can triangulate the position of the invasive device 18 with respect to the skin patches 20. It may be advantageous to space the skin patches 20 apart from each other to enable a more precise triangulation of the invasive device 18. According to other embodiments, just a single skin patch 20 may be attached to the patient 250. The single skin patch 20 may include 3 or more transducer elements. The processing unit 12 may then determine the location of the invasive device 18 based on the timing difference associated with signals from each of the transducer elements attached to the single skin patch 20.

At step 214, a representation of the invasive device, is shown on the image generated from the non-ultrasound data. According to an exemplary embodiment, the non-ultrasound data may be x-ray data and the representation of the invasive device may be an icon of the invasive device 18. As described hereinabove, ultrasound position signals are transmitted from either the invasive device 18 to the transducer elements 136 attached to the one or more skin patches 20, or the ultrasound position signals are transmitted from the transducer elements 136 attached to the one or more skin patches 20 to the invasive device 18. The ultrasound position signals associated with each of the transducer elements 136 are either assigned unique signatures or they are transmitted at different times for purposes of differentiation by the processing unit 116. Based on the time it takes to receive each of the ultrasound position signals, the processing unit 116 can calculate a distance between the invasive device 18 and the specific transducer element 136 attached to a skin patch 20. The processing unit 116 may then determine the position of the invasive device 18 based on the calculated distance of each transducer element 136 from the invasive device 18. The invasive device 18 may include multiple transducer elements as well. The processing unit 116 may calculate distance from each transducer element 136 to multiple transducer elements 136 on the invasive device 18 in order to determine an orientation of the invasive device 18 as well as a position. The representation of the invasive device 18 may be positioned on the non-ultrasound image in a manner consistent with the orientation of the invasive device 18 in the patient's body.

At step 216, the processing unit 12 determines whether it is desired to update the position of the invasive device 18. The processing unit 12 may make the determination at step 216 based on whether or not the processing unit 12 has received updated ultrasound position signals. The method 200 may, for example, return to step 210 if additional ultrasound position signals have been received. The processing unit 12 may then iteratively perform steps 210, 212, 214, and 216 each time additional ultrasound position signals are received. According to an embodiment, ultrasound position signals may be transmitted at a rate of approximately 20 times per second. Therefore, according to an exemplary embodiment, the method 200 may iteratively cycle through steps 210, 212, 214, and 216 many times per second. If it is not desired to update the position of the invasive device at step 216, the method 200 stops.

By iteratively performing steps 210, 212, 214, and 216, the method 200 results in the display of a real-time position of the invasive device 18 with respect to a non-ultrasound image. Embodiments may update the representation of the invasive device many times per second, resulting in a very accurately positioned representation of the invasive device on the non-ultrasound image without exposing the patient or clinician to additional ionizing radiation.

Referring primarily to FIGS. 2 and 9, the method 200 will be described according to an embodiment where the invasive device being tracked comprises an ultrasound probe. Steps 202, 204, 206, and 208 may be performed in a manner similar to that described in detail hereinabove. As such, steps 202, 204, 206, and 208 will not be described again At step 208, a processing unit, such as the processing unit 116 shown in FIG. 2, generates an image based on the non-ultrasound data. The non-ultrasound data may also be accessed from a memory or database by a processing unit such as processing unit 116. According to an exemplary embodiment, the image may comprise an X-ray image. At step 210, the ultrasound position signals are communicated between the ultrasound probe 105, and the transducer elements 136 attached to the skin patches 20. The ultrasound position signals may be communicated according to several different schemes. According to an embodiment, the ultrasound probe 105 may transmit the ultrasound position signals which are then received by the skin patches 20. The ultrasound position signals may, for instance, comprise omnidirectional echoes that are completely unfocused. These ultrasound position signals would be special echoes that are not used to acquire ultrasound imaging data. The ultrasound position signals may be interleaved with echoes transmitted in order to acquire image data. The ultrasound position signals used for determining the position of the ultrasound probe 105 may be transmitted at a rate of 10-30 frames per second according to an exemplary embodiment. It should be appreciated that embodiments may transmit ultrasound position signals at rates both slower than 10 frames per second and faster than 30 frames per second according to other embodiments.

According to an embodiment, the localization system 101 (shown in FIG. 2) the ultrasound pulses used to acquire the ultrasound image may be used as the ultrasound position signals. The same echo pulses used to acquire ultrasound image data are used to determine the position of the ultrasound probe 105 with respect to the skin patches 20. Since the ultrasound pulses used to acquire ultrasound images data are typically focused ultrasound beams, it may be important to position the skin patches 20 so that they are in the field-of-view of the ultrasound probe 105. Using the same echoes to acquire both image data and position information allows the system 90 to determine the position of the probe 105 without adding to the length of a standard image acquisition. This allows for the same frame-rate and image quality as in a conventional ultrasound acquisition with the additional benefit of acquiring ultrasound position signals that can be used to determine the position of the ultrasound probe 105.

According to an embodiment, the ultrasound transducer modules 128 attached to each of the skin patches 20 may be adapted to transmit the ultrasound position signals. The ultrasound position signals may then be received by the ultrasound probe 105. Each transducer element 136 attached to the skin patches 20 may have a unique signature or time difference in order to associate data with a particular transducer element 136 on the skin patch. The transducer elements may be assigned unique signatures by adjusting variables such as pulse shape, pulse length, and frequency. The ultrasound position signals may also be sent from the transducer elements 136 sequentially. In other words, each ultrasound position signal may be sent by a specific transducer element 136 and received by the ultrasound probe 105 before the next ultrasound position signal is transmitted. It is not necessary to apply unique signatures to each transducer element 136 if the position signals are transmitted in a serial manner, but the total time required is greater than if the unique signatures are used and the ultrasound position signals are transmitted in parallel.

According to an embodiment, ultrasound position signals may be transmitted from both the ultrasound probe 105 and the skin patches 20. Or, the ultrasound probe 105 may be used to acquire ultrasound data and the ultrasound position signals may be transmitted from the transducer elements 136 attached to the skin patches 20. If the transducer elements 136 attached to the skin patches are assigned unique signatures, the processing unit 116 may use techniques including Fourier analysis in order to separate the different signals and associate the correct timing information with the appropriate ultrasound transducers 136.

According to an embodiment, the ultrasound probe 105 may comprise a TEE probe. It should be appreciated by those skilled in the art that in other embodiments a different type of invasive device may be used in place of the ultrasound probe 105. For example, FIG. 11 is a schematic representation of a catheter 260 in accordance with an embodiment. The catheter 260 includes a transducer array 262 according to an embodiment. The transducer array 262 includes a plurality of transducer elements (not shown) according to an embodiment. It should be appreciated that the transducer array 262 may function like the array 106 in the ultrasound probe 105 for communicating ultrasound position signals with the transducer elements 136 on the skin patches 20. According to other embodiments, the invasive device may only include a single transducer element for communicating ultrasound position signals with the transducer elements 136 on the skin patches 20.

At step 212, a processing unit, such as the processing unit 116, determines a position of the probe 105 with respect to the image. As previously described, the image is based on non-ultrasound data and the non-ultrasound data was acquired from a region or volume including the skin patches 20. Each of the skin patches 20 includes a fiducial marker 138 that may be clearly identified by the processing unit 116 in the non-ultrasound data or image. As described with respect to step 210, ultrasound position signals are communicated between the probe 105 and the transducer elements 136 attached to the skin patches 20. The processing unit 116 may determine the position of the ultrasound probe 105 with respect to the skin patches 20 based on the time it takes to receive communicate the ultrasound position signal from the ultrasound probe 105 and each respective transducer element 136 on the skin patches 20. As long as at least three of the transducer elements 136 are positioned in a different three dimensional position with respect to the ultrasound probe 105 being tracked, the processing unit 116 can triangulate the position of the ultrasound probe 105 with respect to the skin patches 20. It may be advantageous to space the skin patches 20 apart from each other to enable a more precise triangulation of the invasive device. According to other embodiments, just a single skin patch 20 may be attached to the patient 250. The single skin patch 20 may include 3 or more transducer elements. The processing unit 116 may then determine the location of the ultrasound probe 105 based on the timing difference associated with signals from each of the transducer elements attached to the single skin patch 20.

At step 214, a representation of the probe 105 is shown on the image generated from the non-ultrasound data. According to an exemplary embodiment, the non-ultrasound data may be x-ray data and the representation of the ultrasound probe 105 may be an icon of the invasive device. As described hereinabove, ultrasound position signals are transmitted from either the ultrasound probe 105 to the transducer elements attached to the one or more skin patches or the ultrasound position signals are transmitted from the transducer elements attached to the one or more skin patches to ultrasound probe 105. The ultrasound position signals associated with each of the transducer elements 136 are either assigned unique signatures or they are transmitted at different times for purposes of differentiation by the processing unit 116. Based on the time it takes to receive each of the ultrasound position signals, the processing unit 116 can calculate a distance between the ultrasound probe 105 and the specific transducer element 136 attached to a skin patch 20. The processing unit 116 may then determine the position of the ultrasound probe 105 based on the calculated distance of each transducer element 136 from the invasive device. The ultrasound probe 105 may include multiple transducer elements as well. The processing unit 116 may calculate distance from each transducer element 136 to multiple transducer elements on the invasive device in order to determine an orientation of the ultrasound probe 105 as well as a position. The representation of the ultrasound probe 105 may be positioned on the non-ultrasound image in a manner consistent with the orientation of the ultrasound probe 105 in the patient's body.

At step 216, the processing unit 116 determines whether it is desired to update the position of the ultrasound probe 105. The processing unit 116 may make the determination at step 216 based on whether or not the processing unit 116 has received updated ultrasound position signals. The method 200 may, for example, return to step 210 if additional ultrasound position signals have been received. The processing unit 116 may then iteratively perform steps 210, 212, 214, and 216 each time additional ultrasound position signals are received. According to an embodiment, ultrasound position signals may be transmitted at a rate of approximately 20 times per second. Therefore, according to an exemplary embodiment, the method 200 may iteratively cycle through steps 210, 212, 214, and 216 20 times per second. If it is not desired to update the position of the ultrasound probe 105 at step 216, the method 200 stops.

By iteratively performing steps 210, 212, 214, and 216, the method 200 results in the display of a real-time position of the ultrasound probe 105 with respect to a non-ultrasound image. Embodiments may update the representation of the invasive device many times per second, resulting in a very accurately positioned representation of the ultrasound probe 105 on the non-ultrasound image.

Images from different imaging modalities have different strengths and weaknesses. A different imaging modality may be selected for the non-ultrasound image depending upon the type of procedure being performed and the type of invasive device being inserted into the patient. Oftentimes, X-ray based modalities, such as X-ray, X-ray fluoroscopy, and CT may be selected to use in order to guide a procedure since they have the potential to be anatomically accurate with excellent resolution. The method 200 enables the display of a high-resolution reference image, such as an X-ray image, with real-time feedback regarding the position of the invasive device 18. The method 200 results in the display of a representation of the invasive device 18 on the non-ultrasound image that updates in real-time. Additionally, the method 200 allows for real-time feedback regarding the position and orientation of the invasive device without exposing the patient to additional ionizing radiation. The clinician is able to manipulate and adjust the position of the invasive device 18 while the method 200 is being performed. The clinician benefits from being able to obtain accurate real-time position feedback without exposing the patient to additional dose. The clinician further benefits because the non-ultrasound image used with method 200 may be selected based on any specific criterion. In other words, the clinician may use an image that has benefits such as increased anatomical accuracy, higher resolution, better contrast, or any other image quality to help the clinician to accurately position the invasive device within the patient.

FIG. 11 is a schematic representation of a catheter 260 in accordance with an embodiment of this invention. The catheter 260 includes a transducer module 262. The transducer module 262 may include one or more transducer elements configured to transmit and/or receive ultrasound position signals. The transducer module 262 can communicate with one or more skin patches, such as the skin patches 20 shown in FIG. 10.

Figure 12:
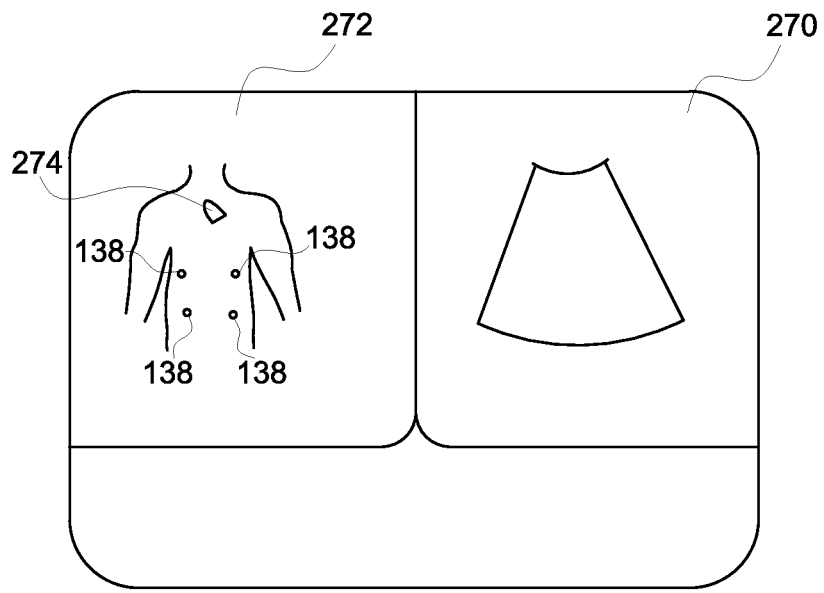
FIG. 12 is a schematic representation of a display format in accordance with an embodiment.

The processing unit 116 may display both the ultrasound image and the non-ultrasound image at the same time according to an embodiment. FIG. 12 is a schematic representation of a display format that may be used in accordance with an embodiment. FIG. 12 is a representation of a technique for displaying an ultrasound image 270 and a non-ultrasound image 272 as a side-by-side image. The ultrasound image 270 may include a real-time image acquired from an ultrasound probe. The non-ultrasound image 272 may include a previously acquired (i.e. not real-time) image acquired with another imaging modality. According to an exemplary embodiment, the non-ultrasound image may comprise an X-ray image. The fiducial markers 138 are easily visible on the non-ultrasound image 272. The non-ultrasound image 272 also includes a representation 274 of the invasive device, which can be an ultrasound probe according to the embodiment shown in FIG. 21. The position of the representation 274 on the non-ultrasound image may be adjusted in real-time in order to reflect the real-time position of the ultrasound probe 105. The side-by side image allows the clinician to quickly and clearly understand the real-time position of the invasive device. Additionally, for embodiments where the invasive device is an ultrasound probe, the clinician can clearly see the position and orientation of the ultrasound probe with respect to the patient's anatomy represented in the non-ultrasound image in real-time.

Figure 13:
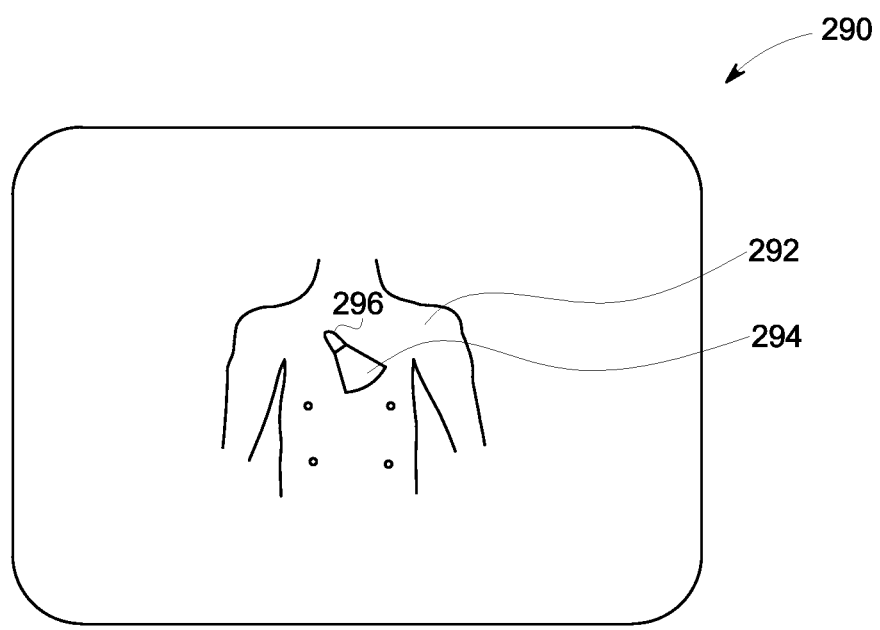
FIG. 13 is a schematic representation of a display format in accordance with an embodiment.

FIG. 13 is a schematic representation of a display format in accordance with an embodiment. FIG. 13 is a fused image in accordance with an embodiment. In FIG. 13 includes a non-ultrasound image 292 combined with an ultrasound image 294. According to an embodiment, the ultrasound image 294 may be superimposed on the non-ultrasound image. According to other embodiments, the ultrasound image may replace data in the non-ultrasound image 292. The fused image 290 may include a representation 296 of the invasive device 18. The position of the representation 296, which may be an icon, can be adjusted in real-time by the processing unit 116 to reflect the real-time position of the invasive device 18. The fused image 290 allows the clinician to quickly and clearly understand the real-time position of the invasive device 18. Additionally, for embodiments where the invasive device 18 is an ultrasound probe 105, the clinician can clearly see the position and orientation of the ultrasound probe 105 with respect to the patient's anatomy represented in the non-ultrasound image in real-time.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A system for tracking an invasive device, the system comprising:
    an ultrasound probe configured to be inserted into a patient's body, the ultrasound probe comprising an array including a plurality of transducer elements, wherein the array is configured both for acquiring ultrasound image data and for tracking a position of the ultrasound probe;
    a display device;
    a localization system comprising:
        a substrate configured to be externally attached to the patient;
        an ultrasound transducer module comprising at least one transducer element attached to the substrate, where the ultrasound transducer module is configured to communicate ultrasound signals with the array; and
        a connector device electrically connected to the ultrasound transducer module; and
    a processing unit in electronic communication with the ultrasound transducer module, the display device and the ultrasound probe, wherein the processor is configured to:
    determine a position of the ultrasound probe based on the ultrasound signals communicated between the array and the at least one transducer element attached to the substrate;
    generate an ultrasound image based on the ultrasound image data acquired by the array;
    display the ultrasound image on the display device; and
    display the position of the ultrasound probe on the display device based on the ultrasound signals communicated between the array and the at least one transducer element attached to the substrate.

2. The system of claim 1, wherein the array is configured to transmit the ultrasound signals to the ultrasound transducer module.

3. The system of claim 2, wherein the processing unit is configured to use the ultrasound signals both to generate the ultrasound image and to determine the position of the ultrasound probe.

4. The system of claim 1, wherein the ultrasound transducer module is configured to transmit the ultrasound signals to the array.

5. The system of claim 1, wherein the array is configured both to transmit a first subset of ultrasound signals to the ultrasound transducer module and to receive a second subset of the ultrasound signals from the ultrasound transducer module, and wherein the processing unit is configured to determine the position of the probe based both on the first subset of the ultrasound signals transmitted from the array to the ultrasound transducer module and on the second subset of the ultrasound signals transmitted from the ultrasound transducer module to the array.

6. The system of claim 1, wherein the array is configured to transmit a second plurality of ultrasound signals to generate the ultrasound image data, where the second plurality of ultrasound signals is different than the ultrasound signals used to determine the position of the ultrasound probe.

7. The system of claim 6, wherein the array is configured to acquire the ultrasound signals and the second plurality of ultrasound signals by interleaving the ultrasound signals with the second plurality of ultrasound signals.

8. The system of claim 1, wherein the substrate includes an adhesive backing configured to be attached to the patient.

9. The system of claim 1, wherein the localization system further comprises a fiducial marker that is configured to be detectable by a non-ultrasound modality.

10. The system of claim 9, wherein the processing unit is further configured to receive a non-ultrasound image, and wherein the processing unit is configured to display the position of the ultrasound probe with respect to the non-ultrasound image on the display device.

11. The system of claim 1, wherein the transducer module comprises a plurality of transducer elements.

12. A method of tracking a position of a probe, the method comprising:
    attaching a first plurality of transducer elements to the outside of a patient:
    positioning an ultrasound probe inside the patient where the ultrasound probe comprises an array including a second plurality of transducer elements;
    communicating ultrasound signals between the array and the first plurality of transducer elements;
    determining with a processing unit a position of the ultrasound probe based on the ultrasound signals communicated between the array and the first plurality of transducer elements, wherein the array is further configured to acquire ultrasound image data with the ultrasound signals; and
    displaying the position of the ultrasound probe on a display device.

13. The method of claim 12, further comprising receiving a non-ultrasound image of the patient, registering the position of the ultrasound probe to the non-ultrasound image, and wherein displaying the position of the ultrasound probe comprises displaying the position of the ultrasound probe with respect to the non-ultrasound image.

14. The method of claim 13, wherein registering the position of the ultrasound probe to the non-ultrasound image comprises using a position of a fiducial marker that is attached to an ultrasound transducer module with at least one of the first plurality of transducer elements.

15. The method of claim 13, wherein the non-ultrasound image comprises an X-ray image or a CT image.

16. A method of tracking a position of a probe, the method comprising:
attaching a first plurality of transducer elements to the outside of a patient;
positioning an ultrasound probe inside the patient, where the ultrasound probe comprises an array including a second plurality of transducer elements,
communicating ultrasound signals between the array and the first plurality of transducer elements;
determining with a processing unit a position of the ultrasound probe based on the ultrasound signals communicated between the array and the first plurality of transducer elements; and
displaying the position of the ultrasound probe on a display device,
wherein the array is configured to acquire ultrasound image data with a second plurality of ultrasound signals that are different than the ultrasound signals.

17. The method of claim 12, wherein the first plurality of transducer elements are attached to one or more skin patches and each of the one or more skin patches is attached to the patient via an adhesive backing.

18. The method of claim 16, further comprising receiving a non-ultrasound image of the patient, registering the position of the ultrasound probe to the non-ultrasound image.

19. The method of claim 18, wherein registering the position of the ultrasound probe to the non-ultrasound image comprises using a position of a fiducial marker that is attached to an ultrasound transducer module with at least one of the first plurality of transducer elements.

20. The method of claim 18, wherein the non-ultrasound image comprises an X-ray image or a CT image.

21. The method of claim 16, wherein the first plurality of transducer elements are attached to one or more skin patches and each of the one or more skin patches is attached to the patient via an adhesive backing.

\* \* \* \* \*